United States Patent [19]

Chandra et al.

[11] Patent Number: 4,631,310
[45] Date of Patent: Dec. 23, 1986

[54] PLATINUM (O) ALKYNE COMPLEXES AND A METHOD FOR THEIR PREPARATION

[75] Inventors: Grish Chandra; Peter Y. Kwai Lo, both of Midland, Mich.

[73] Assignee: Dow Corning Corporation, Midland, Mich.

[21] Appl. No.: 824,041

[22] Filed: Jan. 30, 1986

Related U.S. Application Data

[62] Division of Ser. No. 641,903, Aug. 20, 1984, Pat. No. 4,603,215.

[51] Int. Cl.[4] ............................................. C08L 83/04
[52] U.S. Cl. .................................... 524/862; 524/861; 528/15; 528/31; 528/32; 528/33; 525/478; 525/479; 556/136
[58] Field of Search ................... 556/136; 528/15, 31, 528/32, 33; 525/478, 479; 524/862, 861

[56] References Cited

U.S. PATENT DOCUMENTS

| 3,419,593 | 12/1968 | Willing | 528/15 |
| 3,775,452 | 11/1973 | Karstedt | 528/15 |
| 4,108,833 | 8/1978 | Hatanaka et al. | 528/15 |
| 4,256,616 | 3/1981 | Hatanaka et al. | 528/15 |

Primary Examiner—Melvyn I. Marquis
Attorney, Agent, or Firm—George A. Grindahl

[57] ABSTRACT

A simplified method of manufacture for platinum (O) alkyne complexes is disclosed, as well as novel platinum (O) alkyne complexes per se. The complexes are made by reacting platinum-vinylsiloxane complexes with alkynes. The complexes are used in hydrosilylation, hydrogenation, isomerization and oligomerization reactions. Curable silicones using these platinum (O) alkyne complexes as curing catalysts are also disclosed.

13 Claims, No Drawings

PLATINUM (O) ALKYNE COMPLEXES AND A METHOD FOR THEIR PREPARATION

This is a division of co-pending application Ser. No. 641,903, filed Aug. 20, 1984, now U.S. Pat. No. 4,603,215.

BACKGROUND OF THE INVENTION

This invention relates to certain novel platinum (O) alkyne complexes and to a novel method of preparing them. By platinum (O) alkyne complexes it is meant herein organometallic platinum complexes with acetylene derivatives as ligands, wherein the platinum atom has a formal oxidation state of zero, as measured by cyclic voltammetry.

Platinum (O) alkyne complexes in general are useful as hydrosilylation catalysts, hydrogenation catalysts, and isomerization catalysts for olefins and alkynes.

Platinum (O) alkyne complexes have a number of advantages over the well known platinum catalyst $H_2PtCl_6 \cdot (H_2O)_x$, hereinafter referred to as hexachloroplatinic acid. For example platinum (O) alkyne complexes tend to be more compatible with the reactants they are called upon to catalyze. The platinum (O) alkyne complexes are thus more effective, since it is not necessary to provide excess amounts to make up for losses due to precipitation.

Additionally, platinum (O) alkyne complexes are inherently more chemically stable then hexachloroplatinic acid, especially in the presence of moisture.

The synthesis of platinum (O) alkyne complexes is known. For example, F. Gordon A. Stone, Ligand-Free Platinum Compounds, Acc. Chem. Res. 1981, 14, 317-327, describes the synthesis of platinum (O) alkyne complexes using platinum bis(cyclooctadiene) complexes. Unfortunately, the cyclooctadiene complex itself is difficult to make, involving sensitive intermediates which require special handling. These platinum bis(cycloocatadiene) complexes are much more suitable for laboratory preparations than industrial processes.

N. Boag et al., J.C.S. Dalton (1980) pg. 2170 et seq. describe a number of platinum (O) alkyne complexes synthesized via platinum bis(cyclooctadiene) complexes, and platinum tris(ethylene) complexes.

None of the above references describes a method for the synthesis of platinum (O) alkyne complexes that can be practiced without special handling precautions for the intermediates. Moreover, none of the above references disclose the complexes:

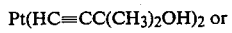 or

$C_6H_5$ is to be taken throughout this specification and the appended claims as representing the phenyl radical, i.e.

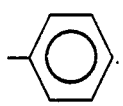

SUMMARY OF THE INVENTION

It is an object of this invention to provide a simple method for making platinum (O) alkyne complexes. It is a further object to provide new hydrosilylation and hydrogenation catalysts.

These objects and others are attained by the method and compositions of the present invention. The method of the present invention comprises contacting an alkyne with a platinum-vinylsiloxane complex to provide a platinum (O) alkyne complex. In other aspects, the present invention relates to certain specific platinum (O) alkyne complexes and their use.

DETAILED DESCRIPTION OF THE INVENTION

The present invention relates to the compound having the formula $Pt(HC \equiv CC(CH_3)_2OH)_2$. The present invention further relates to the compound having the formula . The present invention further relates to a method for making platinum (O) alkyne complexes, said method comprising contacting an alkyne with a platinum-vinylsiloxane complex.

In the method of the present invention, an alkyne is contacted with a platinum-vinylsiloxane complex. The platinum-vinylsiloxane complex is the reaction product of hexachloroplatinic acid and a vinylsiloxane having the general unit formula $$X_aR_nSiO_{(4-a-n)/2},$$

wherein X is a hydrolyzable radical; R is a monovalent hydrocarbon radical; each a has a value of 0 or 1; each n has a value of 1, 2, or 3; the sum of the values of a and n has a maximum value of 3; and there is at least one R unit in said vinylsiloxane having the formula $CH_2=CH-$.

Platinum-vinylsiloxane compounds have been described in U.S. Pat. No. 3,419,593, issued Dec. 31, 1968 to David N. Willing, the specification of which patent is hereby incorporated herein to further teach a method for making suitable platinum-vinylsiloxane complexes. U.S. Pat. No. 3,775,452, issued Nov. 27, 1973 to Karstedt also disclose methods for making suitable platinum-vinylsiloxane complexes.

In general, platinum-vinylsiloxane complexes are made by contacting a vinylsiloxane as described above with a suitable platinum compound such as hexachloroplatinic acid. Hexachloroplatinic acid is well known and widely available commercially.

R in the above general unit formula for the vinylsiloxane is a monovalent hydrocarbon radical. Thus, R can be an alkyl radical, such as methyl, ethyl, propyl or butyl; an aryl radical such as phenyl or naphthyl; a cycloalkyl radical, such as cyclohexyl, cycloheptyl, and the like; an alkenyl radical, such as vinyl or allyl; or a cycloalkenyl radical, such as cyclohexenyl, cycloheptenyl and the like. At least one R of each vinylsiloxane, on average, must be a vinyl radical.

X in the above general formula is a hydrolyzable radical. For example, X can be a halogen atom, such as F, Cl, Br, or I; an alkoxy or aryloxy radical, such as $-OCH_3$, $-OC_2H_5$, $-OC_3H_7$, $-OC_6H_5$, and the like; a carboxy radical, such as acetyl, propionyl, benzoyl, cyclohexanoyl, and the like; and other hydrolyzable groups known in organosilicon chemistry.

The vinylsiloxane can be linear, branched, or cyclic in structure. Examples of appropriate vinylsiloxanes include the following. The term Vi in the following examples of vinylsiloxanes represents the $CH_2=CH-$ radical; the term Me represents the $CH_3-$ radical.

ViMe$_2$SiOSiMe$_2$Vi; ViMe$_2$SiO(SiMeViO)$_7$SiMe$_2$Vi;

ViMe$_2$SiO(SiMeO)$_3$SiMe$_3$
|
OSiMe$_3$ (MeViSiO)$_3$; (MeViSiO)$_4$, the last two formulae representing cyclosiloxanes; and other structures.

Briefly, platinum-vinylsiloxane complexes can be made by contacting the vinylsiloxane with hexachloroplatinic acid. Heating can accelerate the formation of the platinum-vinylsiloxane complex.

Alkynes suitable for reacting with the platinum-vinyl-siloxane complex are well known and readily available. Suitable alkynes are described by the general formula R'C≡CR', wherein each R' independently represents a monovalent hydrocarbon radical, a hydride radical, with the proviso that only one R' can be a hydride radical, or a monovalent hydrocarbon radical substituted with a hydroxyl radical. More preferably, each R' is selected from the group consisting of H; —C(CH$_3$)$_2$(OH); —C(CH$_3$)(C$_2$H$_5$)(OH); —C(C$_2$H$_5$)$_2$(OH); —C(CH$_3$)(C$_3$H$_7$)(OH); —C(C$_5$H$_{11}$)(CH$_3$)(OH); —C(C$_2$H$_5$)(C$_3$H$_7$)(OH);

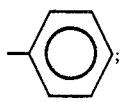

—C(CH$_3$)$_3$; —Si(CH$_3$)$_3$; —(C$_6$H$_4$CH$_3$); and

Many suitable alkynes are commercially available. Alternatively, suitable alkynes can be made by dehydrohalogenation of appropriately substituted vicinal dialkyl halides; by reaction of sodium acetylide with appropriate alkyl halides; and by other known methods of synthesizing alkynes.

The method of the present invention is carried out by contacting an alkyne, as defined above, with a platinum-vinylsiloxane complex, also defined above.

The contacting referred to is done by simply exposing the two reactants to one another as by simply mixing. Mixing can be accomplished manually, by placing the two reactants in a single vessel and swirling or shaking. More preferably, mixing is accomplished with a mechanical stirrer or mixer.

The contacting can be done with the two reactants neat, or it can be done in a suitable solvent. The solvent can be polar or non-polar. Solvents which are known to complex with platinum, or that are discovered to complex with platinum, should be avoided.

If a solvent is used, it is highly preferred to select a solvent in which the reactants are soluble and in which the product, the platinum (O) alkyne complex, is insoluble. If such a solvent is used, the product will precipitate, thus facilitating isolation of the product.

Preferably, 2 moles of the alkyne are provided for each mole of platinum present. However, it may be beneficial in some circumstances to provide partial complexes, such as platinum-alkyne-vinylsiloxane complexes. The method of providing such complexes by furnishing less than 2 moles of alkyne for each mole of platinum is encompassed by the method of the present invention.

Similarly, mixed complexes may be formed by providing two or more different alkynes conjointly. Thus, for example, reacting one mole of platinum with one mole of HC≡CC(CH$_3$)$_2$OH and simultaneously with one mole of C$_6$H$_5$C≡CC(CH$_3$)(C$_6$H$_5$)(OH) will result in a distribution of products including Pt(HC≡CC(CH$_3$)$_2$OH)$_2$ Pt(C$_6$H$_5$C≡CC(CH$_3$)(C$_6$H$_5$)(OH))$_2$, and also the mixed complex, Pt(HC≡CC(CH$_3$)$_2$OH)((C$_6$H$_5$)C≡CC(CH$_3$)(C$_6$H$_5$)(OH))

The production of mixed complexes with two or more different alkynes is also encompassed by the method of the present invention.

The platinum (O) alkyne complexes resulting from the method of the present invention are useful as catalysts for hydrosilylation reactions; as catalysts for hydrogenation of unsaturated organic compounds or polymers; as catalysts for the isomerization of olefins; as catalysts for the oligomerization of acetylene and other alkynes; as flame retardancy additives for silicone rubber; and in many other applications which require a compatible form of platinum.

The platinum (O) alkyne complexes resulting from the method of the present invention are especially useful as curing catalysts for curable silicone compositions comprising (1) a silicone polymer having at least one unit selected from the group consisting of CH$_2$=CH—Si≡ units and ≡SiOH units;

(2) a silicone polymer having at least one ≡SiH unit; and (3) a platinum (O) alkyne complex formed by contacting an alkyne with a platinum-vinylsiloxane complex.

A curable silicone composition as described above is made by simply mixing the appropriate polymers and platinum (O) alkyne complex together. Simple mixing is accomplished by mixers, such as Myers mixers, sigmoid blade mixers, three-roll mills, two-roll mills, Baker Perkins type mixers, and other known mixers.

Generally from 1 to 99 parts by weight of Component (1), from 1 to 99 parts by weight of Component (2), and a catalytically effective amount of the platinum (O) alkyne complex are used. By catalytically effective amount it is meant herein an amount sufficient to allow the curable composition to be cured in a reasonable amount of time, such as an hour or less, at a reasonable elevated temperature, such as 35° C. or higher.

Catalytically effective amounts of the platinum (O) alkyne complex of the present invention vary from 1 part per million by weight to 0.1% by weight.

More preferably, the amounts of Components (1) and (2) are selected so that approximately equimolar amounts of ≡SiH on the one hand and ≡SiCH=CH$_2$ or ≡SiOH on the other hand are used.

A curable composition as described above is a useful coating material, such as a paper release coating. If a reinforcing filler, such as amorphous silica, is added to the curable composition, a useful elastomer will result upon cure.

The platinum (O) alkyne complexes produced by the method are useful catalysts for both filled and unfilled curable silicone compositions.

The following Examples are here presented to further teach the method of the present invention and the use of the products of the present invention. All parts and percentages in the Examples are by weight unless otherwise specified.

The term Me in the Examples represents the methyl radical. The term Vi in the Examples represents the vinyl radical.

CHARACTERIZATION METHODS

The products of the method of the present invention were characterized by the following methods:

Yield:

This mixture was stirred for 5 hours, after which time the toluene was removed by distillation at a temperature of 20° C. and under reduced pressure. The resulting product was a white solid. The product was washed with pentane and dried under vacuum. The product was identified as Pt(C$_6$H$_5$C≡CC(Me)(C$_6$H$_5$)(OH))$_2$. This product had a melting range of 99° C.–101° C. Other characterization data are found in Table 1.

EXAMPLE 2-4

The procedures of Example 1 were followed for each of the following alkynes:

(Me)$_2$(OH)CC≡CC(Me)$_2$(OH),

C$_6$H$_5$C≡CC$_6$H$_5$, and
HC≡CC(Me$_2$)(OH).

Characterization data are found in Table 1.

TABLE 1

| Example | Platinum (O) alkyne | Yield | Elemental Analysis Calculated | Found | IR C≡C frequency (cm$^{-1}$) |
|---|---|---|---|---|---|
| 1 | Pt(C$_6$H$_5$C≡CCMeC$_6$H$_5$)$_2$<br>　　　　　　　\|<br>　　　　　　　OH | 56.2 | % C: 60.09<br>% H: 4.38 | 59.97<br>4.58 | 1889 |
| 2 | Pt(Me$_2$CC≡CCMe$_2$)$_2$<br>　　　\|　　　\|<br>　　　OH　　OH | 64.2 | % C: 40.03<br>% H: 5.85 | 39.89<br>6.03 | 1889 |
| 3 | Pt(C$_6$H$_5$C≡CC$_6$H$_5$)$_2$ | 56.2 | % C: 60.98<br>% H: 3.57 | 60.75<br>3.63 | 1881 |
| 4 | Pt(HC≡CCMe$_2$OH)$_2$ | 63.4 | % C: 22.04<br>% H: 4.40 | 22.42<br>3.90 | 1620 |

Yields were determined by dividing the weight of the product actually obtained by the weight of product which would result from complete reaction and recovery of product, and multiplying the result of this division by 100%.

Elemental Analysis:

Carbon and hydrogen percentages were determined by the combustion method. The complexes being analyzed were quantitatively burned in oxygen, and the resulting weights of CO$_2$ and H$_2$O were determined. These weights were used to calculate the percentages of carbon and hydrogen originally present in the complex.

INFARED AND NUCLEAR MAGNETIC RESONANCE SPECTROSCOPY

Infared and nuclear magnetic resonance spectra were obtained for each complex in the Examples to help identify the product. The spectra determined were consistent with the reported structures in all cases. The infared vibrational frequency of the acetylene bond is often used in characterizing metal-alkyne complexes. The vibrational frequency of the acetylene bond is reported for each complex in the Examples.

EXAMPLE 1

A platinum-vinylsiloxane complex was first formed by reacting hexachloroplatinic acid with (ViMe$_2$Si)$_2$O. The resulting product was neutralized with NaHCO$_3$ and filtered. The filtrate was 4.02% platinum.

5.4 g of this platinum-vinylsiloxane complex (1.1 mmole of platinum) was added to 14 ml of a toluene solution of C$_6$H$_5$C≡CC(Me)(C$_6$H$_5$)(OH). The 14 ml of solution constituted 2.3 mmoles of the alkyne.

EXAMPLE 5

This Example illustrates the use of a product of the method of the present invention in a hydrosilylation reaction.

11.2 g of 1-octene were heated with 0.0009 g of the platinum (O) alkyne complex of Example 1, at 65° C., for 1 minute. A clear solution resulted. This clear solution was cooled to a temperature of 30° C. MeHSiCl$_2$ was added to the cooled solution in a dropwise manner. A vigorously exothermic reaction resulted. The temperature of the reaction mixture rose to 110° C., and external cooling was applied. After 30 minutes, the stoichiometric amount of MeHSiCl$_2$, 11.5 g, had been added, and the reaction appeared to have stopped.

Gas chromatographic analysis of the product indicated that the major species (84%) of the reaction mixture was n-octyl SiMeCl$_2$.

EXAMPLE 6

50 grams of a 30% toluene solution of a silicone gum containing 2 mole percent vinyl substituted groups was mixed with 0.18 g of the platinum (O) alkyne complex produced in Example 3, and 0.15 g of methylvinylcyclosiloxanes.

10 g of the above mixture was subsequently mixed with 40 g of heptane, and 0.04 g of a silicone polymer having the average formula Me$_3$SiO(MeHSiO)$_{40}$SiMe$_3$.

The resulting mixture was a curable silicone composition of the present invention. This curable silicone composition was coated in a thin layer on a sheet of paper and was exposed for 40 seconds in a 77° C. air-circulating oven.

The coating on the paper was cured: The cured coating did not rub off when rubbed by a finger; it did not smear when rubbed by a finger; and the subsequent adhesion of a piece of adhesive tape pressed upon the coating and removed was not noticeably diminished. The above results are characteristic of a well-cured paper coating.

That which is claimed is:

1. A method for making platinum (O) alkyne complexes, said method comprising mixing an alkyne with a platinum-vinylsiloxane complex.

2. A curable silicone composition comprising
   (1) a silicone polymer having at least one unit selected from the group consisting of $CH_2=CH-Si\equiv$ units and $\equiv SiOH$ units;
   (2) A silicone polymer having at least one $\equiv SiH$ unit; and
   (3) A platinum (O) alkyne complex formed by mixing an alkyne with a platinum-vinylsiloxane complex.

3. A composition as claimed in claim 2 comprising:
   from 1 to 99 parts by weight of component 1;
   from 1 to 99 parts by weight of component 2; and
   a catalytically effective amount of component 3.

4. A composition as claimed in claim 3 further comprising a reinforcing filler.

5. A composition as claimed in claim 4 wherein the reinforcing filler is amorphous.

6. A composition as claimed in claim 2 wherein the platinum (O) alkyne complex is $Pt(C_6H_5C\equiv CC(CH_3)(C_6H_5)(OH))_2$.

7. A composition as claimed in claim 6 comprising:
   from 1 to 99 parts by weight of component 1;
   from 1 to 99 parts by weight of component 2; and
   a catalytically effective amount of component 3.

8. A composition as claimed in claim 7 further comprising a reinforcing filler.

9. A composition as claimed in claim 8 wherein the reinforcing filler is amorphous silica.

10. A composition as claimed in claim 2 wherein the platinum (O) alkyne complex is $Pt(HC\equiv CC(CH_3)_2OH)_2$.

11. A composition as claimed in claim 10 comprising:
    from 1 to 99 parts by weight of component 1;
    from 1 to 99 parts by weight of component 2; and
    a catalytically effective amount of component 3.

12. A composition as claimed in claim 11 further comprising a reinforcing filler.

13. A composition as claimed in claim 12 wherein the reinforcing filler is amorphous silica.

* * * * *